United States Patent
Ogata et al.

[11] Patent Number: 5,807,845
[45] Date of Patent: Sep. 15, 1998

[54] THERAPEUTIC DRUG FOR ACNE VULGARIS

[75] Inventors: Kazumi Ogata, Toyonaka; Takahiro Sakaue, Itami; Sachiko Matsuura, Osaka; Masahito Iemura, Kyoto, all of Japan

[73] Assignee: Senju Pharmaceutical Co., Ltd., Osaka, Japan

[21] Appl. No.: 903,036

[22] Filed: Jul. 29, 1997

[30] Foreign Application Priority Data

Jul. 31, 1996 [JP] Japan .................................. 8-200900

[51] Int. Cl.$^6$ .................................................. A61K 31/665
[52] U.S. Cl. ................................................ 514/100; 514/859
[58] Field of Search ....................................... 514/100, 859

[56] References Cited

PUBLICATIONS

CA 124:220539, Ogata et al, Mar. 6, 1996.

CA 124:212079, Ogata et al, Oct. 23, 1995.

CA 124: 212075, Yoshida et al, Oct. 6, 1995.

Primary Examiner—Rebecca Cook
Attorney, Agent, or Firm—Wenderoth, Lind & Ponack, L.L.P.

[57] ABSTRACT

The present invention provides a pharmaceutical composition for the therapy of acne vulgaris which comprises a phosphoric diester compound of the following formula or a pharmacologically acceptable salt thereof

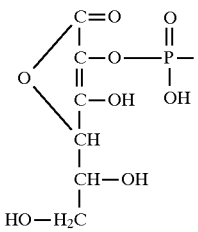

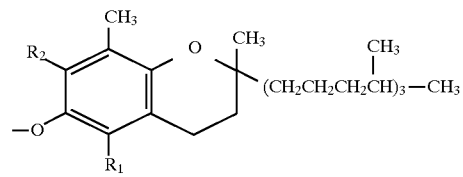

wherein $R_1$ and $R_2$ may be the same or different and each represents hydrogen or methyl.

1 Claim, No Drawings

THERAPEUTIC DRUG FOR ACNE VULGARIS

BACKGROUND OF THE INVENTION

1. Field of the Invention

The present invention relates to a therapeutic drug for acne vulgaris. More particularly, the invention relates to a pharmaceutical composition for the therapy of acne vulgaris which comprises a phosphoric acid ascorbyl tocopheryl diester compound or a pharmacologically acceptable salt thereof.

2. Description of the Prior Art

Acne vulgaris is a chronic lesion of the pilosebaceous gland, which occurs in adolescence. The focus of lesion lies in the sebaceous follicle and is characterized by well-developed sebaceous glands and delicate vellus. Sebaceous follicles are distributed in the skin areas prone to acne vulgaris, such as the forehead, cheeks, back, and central region of the chest. It is known that, in acne vulgaris, the sebaceous gland function has been stimulated by elevation of the concentration of androgens which are sex hormones. Moreover, while the pores of the skin are inhabited by Propionibacterium acnes (P. acnes) which constitutes a normal flora feeding on sebum, this organism multiplies as the sebaceous glands are enlarged. Moreover, P. acnes has high lipolytic activity. Therefore, it is presumed that neutral fats such as glycerides in the sebum which increases as one approaches adolescence are decomposed by P. acnes to release free fatty acids, and that certain kinds of the free fatty acids stimulate the pore epithelium to cause abnormal keratinization, i.e. acne vulgaris.

There are systemic and topical therapies for the treatment of acne vulgaris. The systemic drugs which are most frequently used clinically are antibiotics in the tetracycline (TC) series. In cases not responding to TC antibiotics, erythromycin, which is a macrolide antibiotic, and clindamycin, among others, are used as systemic drugs. For topical therapy, clindamycin and other antibiotics, sulfur, ethyl lactate, salicylic acid, etc. are used.

The present inventors investigated the pharmacological profile of a certain phosphoric diester compound and found that the compound is of use as a therapeutic drug for acne vulgaris. The present invention has been developed on the basis of the above finding.

The present invention provides a novel, effective therapeutic drug for acne vulgaris.

SUMMARY OF THE INVENTION

The present invention, therefore, is directed to a pharmaceutical composition for the therapy of acne vulgaris which comprises a phosphoric diester compound of the following formula or a pharmacologically acceptable salt thereof (hereinafter referred to as compound of the invention)

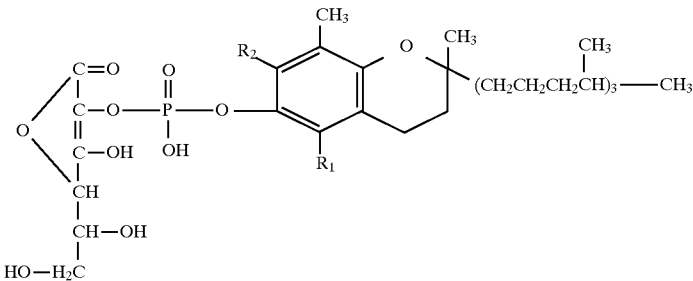

wherein $R_1$ and $R_2$ may be the same or different and each represents hydrogen or methyl.

DETAILED DESCRIPTION OF THE INVENTION

The phosphoric diester compound for use as the therapeutic drug for acne vulgaris according to the present invention is already known to be useful for a variety of applications, such as anticataract drug, a prophylactic and therapeutic drug for climacteric disturbance, a cosmetic ingredient having skin conditioning activity (JP Koho H2-44478), an antioxidant (JP Kokai S63-139972), an anti-ulcer drug (JP Kokai S63-270626), an antiinflammatory agent (JP Koho H1-27044, JP Koho H5-23274), a prophylactic and therapeutic drug for ischemic organ disorders (JP Kokai H2-111722), a Maillard reaction inhibitor (JP Kokai H3-161444), a lipid metabolism improving agent (JP Kokai H6-336435), and a therapeutic drug for epidermal proliferative diseases (JP Kokai H8-3049).

While this compound is known to produce various pharmacological effects such as those mentioned above, it is not known to be therapeutically effective for acne vulgaris.

The compound for use as the therapeutic drug for acne vulgaris according to the present invention can be synthesized by or in accordance with the process described in JP Koho H2-44478 or the process in JP Koho H5-23274.

The compound for use as the therapeutic drug for acne vulgaris according to the present invention may be a free compound or a pharmacologically acceptable salt. The pharmacologically acceptable salt typically includes salts with alkali metals such as sodium, potassium, etc. and salts with alkaline earth metals such as calcium, magnesium, etc., although any other pharmacologically acceptable salt can also be employed.

According to the objective and necessity, the therapeutic drug for acne vulgaris according to the present invention may contain two or more species of the present compound in a suitable combination.

The present compound for use as the active ingredient in the pharmaceutical composition for acne vulgaris according to the present invention is a safe compound with a very low toxicological potential and can therefore be used with advantage for the purposes of the invention [e.g. $LD_{50}$ of L-ascorbyl DL-α-tocopheryl phosphate potassium (hereinafter referred to briefly as EPC-K): oral, 5 g/kg (rat); intravenous, $\geq 100$ mg/kg (rat)].

The therapeutic drug for acne vulgaris according to the present invention can be administered orally or otherwise. The dosage form that can be used includes solid dosage forms such as tablets, granules, powders, capsules, ointments, etc. and various liquid dosage forms. Those dosage forms can be prepared by using the conventional pharmaceutical auxiliaries a such as the excipient, binder, disintegrator, dispersant, reabsorption promoter, buffer, surfactant, solubilizer, preservative, emulsifier, isotonizing agent, stabilizer, and pH control agent in suitable proportions.

The dosage of the present compound as a therapeutic drug for acne vulgaris depends on the species of compound, the patient's age and body weight, the clinical condition to be controlled, and the specific dosage form used. In the case of an oral dosage form, an adult patient is given about 10–1000 mg/dose a few times daily. An ointment preferably contains about 0.01–10 (w/w) % of the compound.

Unless contrary to the object of the invention, the pharmaceutical composition for the therapy of acne vulgaris according to the present invention may further contain other therapeutic drug substances for acne vulgaris and/or ingredients having different kinds of pharmacological efficacy, e.g. antibacterial agents.

EXAMPLES

The following examples and formulation examples are intended to describe the present invention in further detail.

EXAMPLE 1

Inhibitory Effect of the Present Compound on the Increase in Hamster Sebaceous Gland Area It is known that, in acne vulgaris, the sebaceous gland function of the skin is enhanced by elevation of the androgen level. Therefore, the auricular sebaceous glands were expanded by subcutaneous administration of an androgen to hamsters and the inhibitory effect of the present compound on this enlargement was tested.

Experimental Animals

Female Syrian hamsters purchased from SLC Japan were used at the age of 7 weeks.

Test Materials (1) Methanol (control)

(2) 0.2% L-ascorbyl DL-α-tocopheryl phosphate potassium (abbreviation: EPC-K)

(3) Normal group

Method

In 1 ml of sesame oil was dissolved 80 μg of testosterone propionate and the solution was administered subcutaneously to hamsters every other day for 2 weeks to enlarge auricular sebaceous glands. The test material was applied in a volume of 20 μl to the right auricle twice daily for 2 weeks from the beginning of the test. The normal group was subjected to neither treatment. After 2 weeks, the hamsters were sacrificed. The right auricle was bored with a 9 mm-diameter punch and the sebaceous gland area was measured by the whole mount technique. The data were statistically analyzed by Dunnett's test. The level of significance was p<0.05.

References

1) Seki, Taiho. et al., Construction of a hamster model of sebaceous gland hyperfunction (disease model) and the effect of Coptis japonica and berberine chloride on sebaceous glands in the disease model, Journal of Wakan Iyakugaku, 12, 436–437, 1995.

2) Motoyoshi, K. et al., Whole Mount Technique, Jpn. J. Dermatol., 15, 252–256, 1988.

Results

The results are shown in Table 1.

TABLE 1

Inhibitory effect of the compound on the increase in auricular sebaceous gland area

| Group | Area ($\mu m^2$) | % Inhibition |
|---|---|---|
| Methanol | 10282 ± 1425 | — |
| 0.2% EPC-K | 3327 ± 225* | 72.5 |
| Normal group | 686 ± 91 | — |

Each value represents mean ± standard deviation (n = 7–8).
Significantly different vs. control group*; p < 0.01.

It will be apparent from Table 1 that 0.2% EPC-K significantly inhibited the increase in auricular sebaceous gland area by 72.5%. This result indicates that the present compound is of value as a therapeutic drug for acne vulgaris.

EXAMPLE 2

Determination of the Minimal Growth Inhibitory Concentration of the Compound Against Propionibacterium Acnes (P. acnes)

The minimal growth inhibitory concentration (MIC) of the present compound against P. acnes, which is a factor in the onset of acne vulgaris and a member of the normal flora of the skin, was determined.

Test Materials (1) EPC-K (dissolved in distilled water)

Doubling dilutions from 10 mg/ml to $1.953125 \times 10^{-2}$ mg/ml in final concentration (2) dl-α-tocopherol and L-ascorbic acid (dissolved in a mixed solution which consists of HC-60 (trademark, manufactured by NOF corporation) and propyleneglycol)

Dubling dilutions from 5 mg/ml to $7.8125 \times 10^{-2}$ mg/ml in final concentration (3) As control, the mixed solution mentioned above was tested.

Method

This test was performed by the method published by Committee for the Study of Methods for MIC Determination in Anaerobic Bacteria.

A frozen clinically isolated strain of P. acnes was subcultured on GAM agar medium for 3 generations and suspended in saline at about $10^8$ cells/ml. This cell suspension and a 100-fold dilution thereof were used as inocula.

To molten GAM agar medium was added ⅑ volume of the test solution of a varying concentration and, after thorough mixing, sensitivity assay plates ranging from 10 mg/ml to $1.953125 \times 10^{-2}$ mg/ml in final concentration were prepared (plate pH 6.64–7.10). Using a loopful of the inoculum, each plate was streaked and incubated anaerobically at 37° C. for at least 48 hours. The incubated plate was then observed grossly and the lowest concentration causing a definite inhibition of growth was regarded as the MIC.

The inoculum was serially diluted 10-fold down to $10^8$ and GAM medium was inoculated with each dilution. After culture, the number of colonies were similarly countered for confirmation of the cell count.

References

Committee for the Study of Methods for MIC Determination in Anaerobic Bacteria: the method for MIC assays in anaerobic bacteria, Chemotherapy, 27, 559–560, 1979.

Results

The results are shown in Tables 2 and 3.

TABLE 2

Minimum inhibitory concentration of EPC-K against Propionibacterium acnes

| | | Concentration (mg/ml) | | | | | | | | | |
|---|---|---|---|---|---|---|---|---|---|---|---|
| Test material | Cell count | 10.0 | 5.0 | 2.5 | 1.25 | 0.625 | 0.3125 | 0.15625 | $7.8125 \times 10^{-2}$ | $3.90625 \times 10^{-2}$ | $1.953125 \times 10^{-2}$ |
| EPC-K | $10^8$ CFU/ml | – | – | – | – | – | + | + | + | + | + |
| | $10^6$ CFU/ml | – | – | – | – | – | – | + | + | + | + |

The symbol "+" means growth and "–" means growth inhibition.

TABLE 3

Minimum inhibitory concentration of vitamins against Propionibacterium acnes

| | | Concentration (mg/ml) | | | | | | |
|---|---|---|---|---|---|---|---|---|
| Test material | cell count | 5.0 | 2.5 | 1.25 | 0.625 | 0.3125 | 0.15625 | $7.8125 \times 10^{-2}$ |
| dl-α-Tocopherol | $10^8$ CFU/ml | + | + | + | + | + | + | + |
| | $10^6$ CFU/ml | + | + | + | + | + | + | + |
| L-Ascorbic acid | $10^8$ CFU/ml | + | + | + | + | + | + | + |
| | $10^6$ CFU/ml | + | + | + | + | + | + | + |
| Control | $10^8$ CFU/ml | + | + | + | + | + | + | + |
| | $10^6$ CFU/ml | + | + | + | + | + | + | + |

The symbol "+" means growth.

It is apparent from Table 2 that the present compound showed a MIC value of 0.625 mg/ml at the cell count of $10^8$/ml and a MIC value of 0.3125 mg/ml at $10^6$/ml. On the other hand, it is apparent from Table 3 that dl-α-tocopherol and L-ascorbic acid showed a MIC value of not less than 5 mg/ml, respectively. These results indicate that the antibacterial activity of the compound of the present invention is superior to those of dl-α-tocopherol and L-ascorbic acid.

| Formulation Example 1 | |
|---|---|
| Oral Tablets | |
| EPC-K | 100 mg |
| Lactose | 75 mg |
| Starch | 20 mg |
| Polyethylene glycol 6000 | 5 mg |

The above components per tablet are blended in the routine manner. Where necessary, the tablet may be sugar-coated.

| Formulation Example 2 | |
|---|---|
| Ointment | |
| L-ascorbyl DL-α-tocopheryl phosphate sodium (EPC-Na) | 5.0 g |
| Glycerin | 12.0 g |
| Stearyl alcohol | 25.0 g |
| White petrolatum | 25.0 g |
| Methyl p-hydroxybenzoate | 0.025 g |

| Formulation Example 2 | |
|---|---|
| Ointment | |
| Propyl p-hydroxybenzoate | 0.015 g |
| Sterilized pure water | to make 100 g |

The above components are mixed in the routine manner to provide an ointment.

| Formulation Example 3 | |
|---|---|
| Gel | |
| EPC-K | 0.2 g |
| Carboxyvinyl polymer | 1.0 g |
| Triethanolamine | q. s. |
| Propyl p-hydroxybenzoate | 0.014 g |
| Ethanol | 30 ml |
| Sterilized pure water | to make 100 ml |
| | pH 7.0 |

The above components are mixed in the routine manner to provide a gel.

What is claimed is:

1. A method of treating acne vulgaris which comprises administering to a patient in need thereof an effective amount of a phosphoric diester compound of the following formula or a pharmacologically acceptable salt thereof
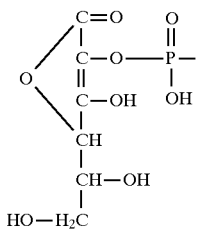
-continued
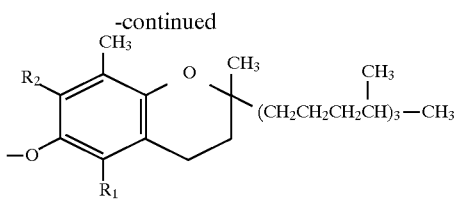
wherein $R_1$ and $R_2$ may be the same or different and each represents hydrogen or methyl.
* * * * *